United States Patent
Denes et al.

(10) Patent No.: US 7,128,816 B2
(45) Date of Patent: Oct. 31, 2006

(54) METHOD AND APPARATUS FOR PRODUCING COLLOIDAL NANOPARTICLES IN A DENSE MEDIUM PLASMA

(75) Inventors: Ferencz S. Denes, Madison, WI (US); Sorin O. Manolache, Madison, WI (US); Noah Hershkowitz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 722 days.

(21) Appl. No.: 09/880,737

(22) Filed: Jun. 13, 2001

(65) Prior Publication Data

US 2002/0037320 A1   Mar. 28, 2002

Related U.S. Application Data

(60) Provisional application No. 60/219,347, filed on Jun. 14, 2000.

(51) Int. Cl.
*B01J 19/08*   (2006.01)

(52) U.S. Cl. ........................ 204/164; 204/165

(58) Field of Classification Search ............... 204/164, 204/165
See application file for complete search history.

(56) References Cited

U.S. PATENT DOCUMENTS

| | | | |
|---|---|---|---|
| 3,169,914 A | 2/1965 | Young et al. | |
| 3,840,750 A | 10/1974 | Davis et al. | |
| 3,954,954 A | 5/1976 | Davis et al. | |
| 4,016,448 A | 4/1977 | Nighan et al. | |
| 4,416,751 A * | 11/1983 | Berkowitz et al. | 204/165 |
| 4,731,515 A * | 3/1988 | Savage et al. | 219/69.17 |
| 4,915,955 A | 4/1990 | Gomori | |
| 5,061,354 A * | 10/1991 | Smith et al. | 204/164 |
| 5,234,723 A | 8/1993 | Babacz | |
| 5,368,724 A | 11/1994 | Ayers et al. | |
| 5,437,858 A | 8/1995 | Hungerbach et al. | |
| 5,534,232 A * | 7/1996 | Denes et al. | 422/186.26 |
| 5,543,133 A | 8/1996 | Swanson et al. | |
| 5,585,020 A | 12/1996 | Becker et al. | |
| 5,655,210 A | 8/1997 | Gregoire et al. | |
| 5,660,465 A * | 8/1997 | Mason | 366/3 |
| 5,766,447 A | 6/1998 | Creijghton | |
| 5,876,663 A | 3/1999 | Laroussi | |
| 5,879,715 A | 3/1999 | Higgins et al. | |
| 5,908,539 A | 6/1999 | Young et al. | |
| 6,027,469 A | 2/2000 | Johnson | |
| 6,054,495 A | 4/2000 | Markowitz et al. | |
| 6,096,564 A | 8/2000 | Denes et al. | |
| 6,187,206 B1 | 2/2001 | Bernier et al. | |
| 6,228,266 B1 | 5/2001 | Shim | |
| 6,264,898 B1 | 7/2001 | Ingram | |

(Continued)

OTHER PUBLICATIONS

What is Colloidal Silver?, web page printout dated Jan. 24, 2000 from http://www.csprosystems.com/whatispg.htm.

(Continued)

*Primary Examiner*—Kishor Mayekar
(74) *Attorney, Agent, or Firm*—Foley & Lardner LLP

(57) ABSTRACT

A method and apparatus is utilized for producing colloidal dispersions of nanoparticles of electrically conducting materials. The colloidal dispersions are produced in a dense media plasma reactor comprising at least one static electrode and at least one rotating electrode. The plasma reaction sputters off minute particles of the electrically conducting material from which the electrodes are made. Methods of using the colloidal dispersions thus made are also described. Colloidal dispersions of silver produced in this manner are highly effective for bactericidal purposes.

33 Claims, 5 Drawing Sheets

U.S. PATENT DOCUMENTS

| | | |
|---|---|---|
| 6,328,898 B1 | 12/2001 | Akiyama et al. |
| 2002/0037320 A1 | 3/2002 | Denes et al. |
| 2002/0074290 A1 | 6/2002 | Jensen |

OTHER PUBLICATIONS

Make Your Own Colloidal Silver, web page printout dated May 16, 2000 from http://www.csprosystems.com/Editorial.htm.

S. Manolache, E.B. Somers, A.C.L. Wong, V. Shamamian, F. Denes, "Dense Medium Plasma Environments . . . A New Approach for the Disinfection of Water," submitted in Oct. 2000 for publication to Water Science and Technology.

Akira Mizuno, et al., "Destruction of Living Cells by Pulsed High-Voltage Application," IEEE Trans. on Industrial Applications, vol. 24, No. 3, May/Jun. 1988, pp. 387-394.

Norman F. Marriott, Principles of Food Sanitation (book), Van Nostrand Reinhold, New York, 1989, pp. 106-109.

George J. Banwart, Basic Food Microbiology (book), Van Nostrand Reinhold, New York, 1989, pp. 682, 684, 694, 695.

Masayuki Sato, et al., "Formation of Chemical Species and Their Effects on Microorganisms Using a Pulsed High-Voltage Discharge In Water," IEEE Trans. on Industrial Applications, vol. 32, No. 1, Jan./Feb. 1996, pp. 106-112.

Sorin Manolache and Ferencz Denes, "Synthesis of Nanoparticles under Cold-Plasma Conditions," Journal of Photopolymer Science and Technology, vol. 13, No. 1, 2000, pp. 51-62, presented at the 17th Conference of Photopolymer Science and Technology, Jun. 27-30, 2000, Chiba, Japan.

Micronic Silver, web page printout dated Jan. 24, 2000 from www.healthstar.com/Pages/MicronicSilver.html.

Clean Water Silver Line, web page printout dated May 16, 2000 from www.cleanwater.com.br/ing/produtos.htm.

Colloidal Silver, web page printout dated Jan. 24, 2000 from http://business.fortunecity.com/mars/476/whatiscs.html.

* cited by examiner

METHOD AND APPARATUS FOR PRODUCING COLLOIDAL NANOPARTICLES IN A DENSE MEDIUM PLASMA

CROSS REFERENCE TO RELATED APPLICATION

This application claims the benefit of provisional patent application No. 60/219,347, filed Jun. 14, 2000, the disclosure of which is incorporated herein by reference.

REFERENCE TO GOVERNMENT RIGHTS

This invention was made with United States government support awarded by the following agencies: DOE DE-FG02-97ER54437. The United States government has certain rights in this invention.

FIELD OF THE INVENTION

The present invention relates to a colloidal suspension of nanoparticles made from electrically conductive materials. More particularly, the present invention relates to a colloidal suspension of electrically conductive material particles having an average diameter of about 1 to 100 nm and the process for making the same. Most particularly, the present invention relates to making such a colloidal suspension of silver nanoparticles.

BACKGROUND OF THE INVENTION

Nanoparticles are important components in the development of catalytic, sensor, aerosol, filter, biomedical, magnetic, dielectric, optical, electronic, structural, ceramic and metallurgical applications. Nanoscale metallic particles exhibit volume and surface effects which are absent in the same material with dimensions in the micron range (i.e., 0.1 micron<particle diameter<1 micron).

The use of colloidal suspensions of silver as antimicrobial agents is well known. Such use is resuming increased importance as antibiotic resistant bacteria become more prolific. Minimizing the silver particle sizes is believed to be important both from the stability of the colloidal suspension and for the efficacy against microbes.

Various processes to produce nanoparticles are known in the prior art. For example, U.S. Pat. No. 5,543,133, issued to Swanson et al., discloses a process of preparing nanoparticulate agents comprising the steps of: (i) preparing a premix of the agent and a surface modifier; and, (ii) subjecting the premix to mechanical means to reduce the particle size of the agent, the mechanical means producing shear, impact, cavitation and attrition.

Likewise, U.S. Pat. No. 5,585,020, issued to Becker et al., teaches a process of producing nanoparticles having a narrow size distribution by exposing microparticles to an energy beam such as a beam of laser light, above the ablation threshold of the microparticles.

Also, U.S. Pat. No. 5,879,750, issued to Higgins et al., teaches a process for producing inorganic nanoparticles by precipitating the inorganic nanoparticles by a precipitating agent for a microemulsion with a continuous and a non-continuous phase and concentrating the precipitated nanoparticles employing an ultrafiltration membrane.

Additionally, U.S. Pat. No. 6,540,495, issued to Markowicz et al., teaches a process for making a powder containing metallic particles comprising the steps of: (i) forming a dispersion of surfactant vesicles in the presence of catalytic metal ions; (ii) adjusting the pH to between 5.0 and 7.0; (iii) mixing the dispersion with a bath containing second metal ions; and; and, (iv) incubating the mixed dispersion at a temperature sufficient to reduce the second metal ions to metal particles having an average diameter between 1 to 100 nm.

CS Pro Systems advertises a high voltage AC processor producing nanoparticles of colloidal silver. The HVAC process is claimed to produce particle sizes between 0.002 to 0.007–9 microns by imposing an AC potential of 10,000 volts across two silver electrodes in a distilled water medium.

The production of large quantities of colloidal silver solutions required for industrial applications, such as water treatment or treatment of biological fluids, are not economical by using the electrolytic approach.

The prior art methods do not provide a simple, convenient, low-cost method for producing colloidal suspensions of electrically conductive particles. It is a hallmark of the current invention to provide such a method.

SUMMARY OF THE INVENTION

A method is disclosed for producing a colloidal dispersion of nanoparticles of at least one conductive material in a dense fluid medium. The method is based on the operation of a modified dense medium plasma (DMP) environment, which allows the initiation of multiple spark discharges in a very intensely stirred liquid media. The method comprises the steps of: providing a reaction vessel for containing the dense fluid medium; charging the dense fluid medium into the reaction vessel; providing a rotatable first electrode comprising a first conductive material, the first electrode immersed within the dense fluid medium; providing a static second electrode comprising a second conductive material, the second electrode immersed within the dense fluid medium and being near to the first electrode; rotating the first electrode such that the dense medium is circulated between the first and second electrodes; and imposing an electric potential between the rotating first electrode and the second electrode to create a discharge zone, the electric field between the electrodes being sufficiently high to dislocate nanoparticles of at least one of the first conductive material or second conductive material from the respective electrode. Preferably, the electrodes are easily interchanged to facilitate changeover between dispersions.

A dense phase plasma discharge apparatus in accordance with the invention may include a chamber forming a reaction vessel for the dense medium. A first electrode is mounted for a rotation about an axis in the chamber and has an end piece which is formed of conductive material with a planar surface. A plurality of pins are mounted in an array projecting from the planar surface. A second electrode is mounted in the chamber and has an end piece of conductive material with a planar surface, with the planar surfaces of the end pieces of the first and second electrodes separated from each other by a gap. The end pieces of the first and second electrodes, including the pins on the one end piece, may be formed of silver for efficiently producing colloidal silver. A motor may be coupled to the first electrode to selectively drive the first electrode in rotation. A magnetic coupling system may be utilized to couple the drive from the motor to the rotating electrode. The pins in the electrode are preferably formed in a spiral array. Rapid rotation of the electrode with the pins therein creates vigorous mixing and cavitation of the dense medium, such as water, between the upper and lower electrodes to enhance the action of the discharges taking place between the electrodes and thereby enhance the production of nanoparticles dislodged from the electrodes from the discharge.

Utilization of the method and apparatus of the invention with silver electrodes may be used to produce colloidal silver which is highly effective as a bactericide and can be used for controlling viruses and spores.

Further objects, features and advantages of the invention will be apparent from the following detailed description when taken in conjunction with the accompanying drawings.

DETAILED DESCRIPTION OF THE PRESENT INVENTION

Figure 1:
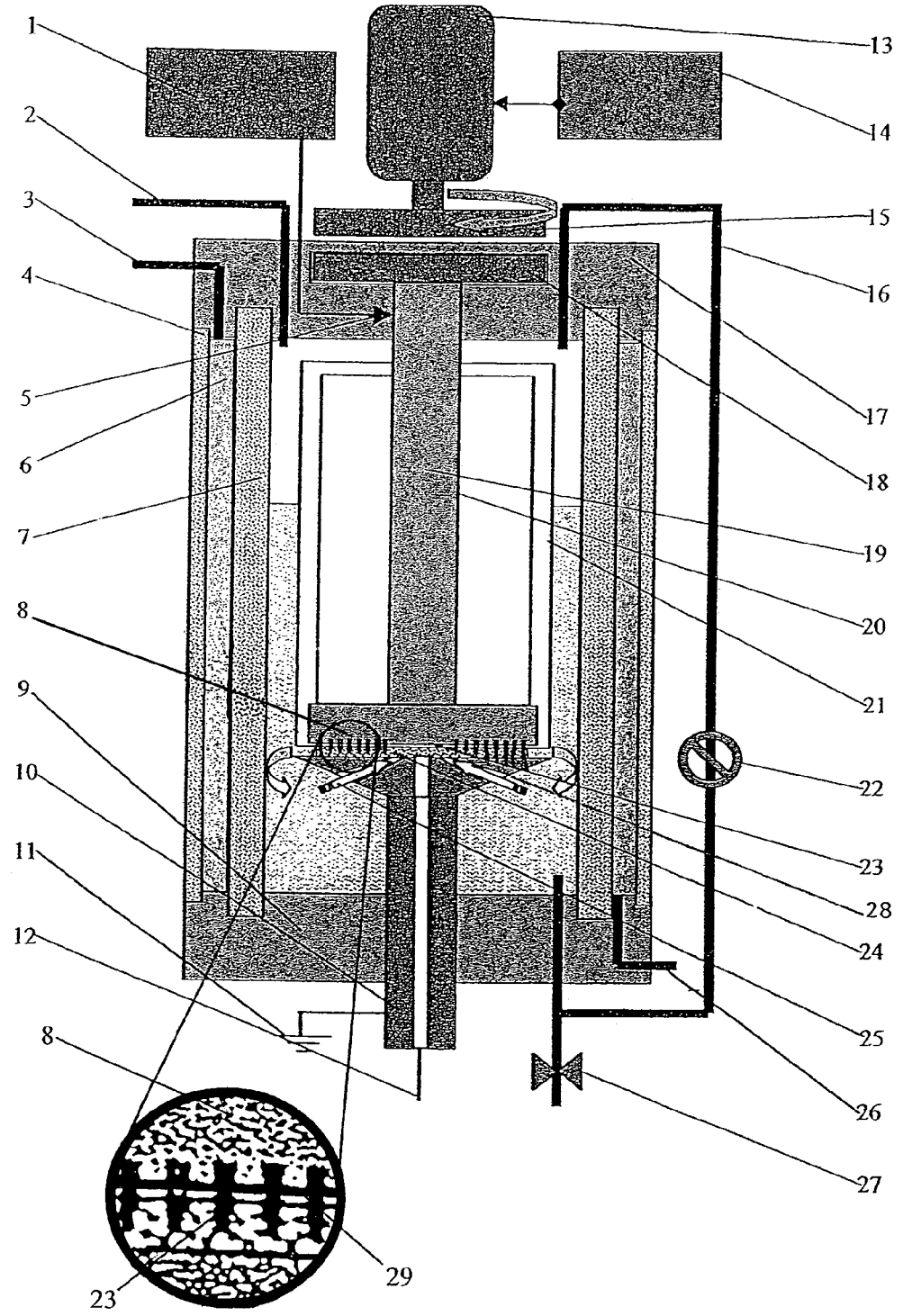
FIG. 1 shows a schematic representation of a dense medium plasma reactor suitable for use in this invention.

As used herein, the term "nanoparticle" refers to particles having an average diameter of less than about 100 nm, preferably less than about 50 nm, more preferably less than about 20 nm, most preferably less than about 10 nm.

As used herein, the terms "electrically conducting material," "conductive material" or "conductor" are interchangeable and refer to a class of bodies incapable of supporting electric strain such that a charge given to a conductor spreads to all parts of the body of the conductor.

The term "dense medium" refers to materials that are liquid at the operating conditions in the plasma reactor.

The term "plasma" is used to identify gaseous complexes which may comprise electrons, positive or negative ions, gaseous atoms and molecules in the ground state or any higher state of excitation including light quanta. The most common method for achieving a plasma state is through an electrical discharge. Electrical discharge plasmas are either "hot," i.e., thermal, or "cold," i.e., nonthermal.

"Hot" (thermal plasma) plasmas comprise gas atoms and electrons which are essentially close to thermal equilibrium with each other. "Hot" plasmas are produced from electrical arcs, plasma jets, and magnetic fields. "Hot" plasmas produced from electrical arcs and plasma jets require equilibrium conditions in which the gas and electron temperatures are very high ($5\times10^3$K) and nearly identical. As a result, most organic molecules and polymers cannot be treated under these conditions because they would be rapidly degraded.

There are also several disadvantages associated with hot plasma synthesis. One main disadvantage is the presence of elevated temperatures of the gas phase and substrate. The elevated temperature requirement limits plasma synthesis to organic reactions, limits high molecular weight depositions, and creates a requirement for costly handling equipment due to the high temperatures generated. Other disadvantages include the predominance of decomposition reactions and the production of non-recyclable gas compositions generated from undesired secondary gas phase recombination reactions.

"Cold" plasmas, which are not at thermal equilibrium, comprise gas atoms at room temperature and electrons at much higher temperatures. This plasma state provides an ambient gas temperature along with electrons which have sufficient kinetic energy to cause the cleavage of chemical bonds. As a result, "cold" plasmas are highly suitable for chemical reactions, such as organic synthesis, polymerizations, surface treatments, and grafting reactions, which involve thermally sensitive materials. "Cold" plasmas are characterized by average electron energies of 1–20 electron Volts and electron densities of $10^9$ to $10^{12}$ cm$^{-3}$. There are two types of "cold" plasmas: 1) the low pressure glow types which are produced by alternating current, direct current, or radio frequency discharges; and 2) the high pressure corona type and barrier discharges produced at electrodes during a high-voltage discharge.

The applicants have found that colloidal suspensions of nanoparticles of electrically conductive materials can be produced by generating a plasma reaction between two electrodes, comprising the desired electrically conductive material(s), which are immersed within a dense fluid medium. Preferably, the dense medium is rapidly recirculated between the two electrodes.

The colloidal nanoparticle dispersion is produced by fine sputtering particles of the electrically conducting material from the electrodes, by the multitudes of (DC or AC) discharges initiated and sustained between the rotating and the stationary electrodes, into the intensely stirred dense medium, which is preferably water.

Advantageously, the electrodes can comprise any desired electrically conductive material. Typically, electrically conducting materials usable in this invention include metals, carbon or combinations thereof. Specific examples of suitable metals include aluminum, antimony, bismuth, copper, gold, iron, lead, molybdenum, nickel, platinum, silver, tin, tungsten, zinc or the rare earths (group IIIB (lanthanide series) of the periodic table as published in *Hawley's Condensed Chemical Dictionary*, 12$^{th}$ ed., front cover). Combinations or alloys of the conductive materials are encompassed within the scope of the current invention, but, preferably, the conductive material is substantially pure. "Substantially pure" means that the resulting nanoparticles have sufficient purity for the desired use. Typically, the electrically conducting material should be at least about 90, preferably at least about 95, more preferably at least about 99 percent pure.

Preferably, the electrodes are constructed of an electrically conducting material which is substantially inert to the dense medium. "Substantially inert" means that the electrically conducting material does not react with or dissolve in an undesirably high rates under the conditions present during the plasma reaction. Preferred examples of suitable materials for the electrodes include carbon, copper, silver, gold, platinum, more preferably silver. If desired, the electrodes may be made from different materials in order to produce a colloidal suspension of more than one electrically conducting material.

Preferably, the electrodes are constructed so as to be easily removed and installed. This easy interchangeability facilitates replacing worn electrodes or changing electrodes to accommodate the production of different colloidal dispersions.

The dense medium may be any liquid having a viscosity low enough to permit rapid circulation of the fluid between the two electrodes. The plasma reaction will decompose the molecules of the dense medium into highly reactive free radicals. As such, the reaction products formed from the dense medium free radicals may be final reaction products or undesirable contaminants to the colloidal solution. An undesirable by-product is any compound that must be removed, due to technical, practical or aesthetic reasons, from the colloidal dispersion prior to use. In most cases, when inorganic/organic hybrid nanoparticle systems are prepared, liquid phase organometallic compounds can be used. The dense medium can be typically selected to avoid the production of undesirable by-products. In the preferred embodiment, the decomposition reaction products of water ($H^+$ and $OH^-$) readily react with each other to reform the water molecule. In contrast, the decomposition reaction products of other dense media, e.g. benzene, are free radicals which may initiate polymerization reactions.

When sole (non-hybrid) nanoparticle systems are required, the plasma should not generate byproducts from dense medium. Preferably, any reaction between the dense medium and the electrically conductive material is slow enough that the nanoparticles in the colloidal dispersion have the desired shelf-life. Most preferably, the dense medium, and any minute quantity of by-product, is non-reactive with the electrically conducting material. "Non-reactive" means that the dense medium and the nanoparticle material do not combine to form a new compound under the operating conditions of the plasma reactor. Examples of usable dense medium liquids include organic solvents, silicon tetrachloride, isobutylene, etc. (in applications where by-products are not undesirable), and water, preferably water.

The electrodes and the dense fluid medium are located within any suitable containment means. The containment means may be open or closed, preferably closed, more preferably a closed pressure vessel. The containment means optionally has means, such as a vacuum pump, to evacuate the containment means. Preferably, the containment means may be pressurized, more preferably pressurized by charging the containment means with an overpressure of inert gas. Preferably, the containment means has means, such as ports, valve, pumps, etc., to charge and discharge the dense medium. The dimensions of the containment means should be sufficient to prevent loss of the dense medium or colloidal dispersion and to provide the volume required for the volume of dense medium and electrodes. Preferably, the containment means has a size and shape to accommodate the desired batch size/throughput rate of the dense medium such that the desired circulation pattern of the dense medium may be obtained without dead spots. Several containment means may be connected in parallel or, preferably, in series, to facilitate continuous production of the colloidal dispersion.

The colloidal dispersions of this invention are conveniently produced in dense medium plasma reactors. An example of such a reactor is disclosed in U.S. Pat. No. 5,534,132 which is incorporated herein by reference. Another example of such a dense medium plasma reactor is shown in FIG. 1. However, one skilled in the art will recognize that any dense medium plasma reactor which comprises at least two electrodes, means for rapidly recirculating the dense medium between the two electrodes and means to provide bubbles within the dense medium circulating between the electrodes is suitable for use in this invention.

A preferred apparatus for producing colloidal nanoparticles in a dense medium is illustrated generally in FIG. 1.

The apparatus of FIG. 1 includes a DC power supply 1, an evacuation tube 2 for gasses, a coolant exit tube 3 and an inlet tube 26, outer and inner glass cylinders 4 and 7 which form part of the chamber for the reaction vessel, an electrical brush contactor 5, and coolant 6 which is enclosed within the volume defined between the outer glass cylinder 4 and the inner glass cylinder 7. An upper electrode 19 may include an end piece 8 having an array of conductive pins 23 in a ceramic holder. The chamber of the reaction vessel is further enclosed by a lower end cap 9 and an upper end cap 17 which are engaged with the glass cylinders 4 and 7 to form an enclosed space for the coolant 6 and an inner chamber defining the reaction vessel. The lower electrode 10 is a non-rotating electrode and is mounted with its end piece adjacent to the end piece of the upper electrode. The lower electrode 10 is electrically connected to a ground 11. A gas inlet tube 12 formed through the lower electrode allows introduction of gas through the electrode into the gas space between the planar faces of the end pieces of the upper and lower electrodes. A motor 13, e.g., an electric motor, hydraulic motor, etc. is controlled by a controller 14 (e.g., digital motor controller) and is coupled via magnetic couplers 15 and 18, which form a magnetic coupling system to the rotating upper electrode 17. The electrode 19 is conductive to conduct power from the power supply 1, as transferred thereto by the brush 5, to the electrically conductive end piece 8 and the pins mounted thereon. The dense medium is supplied to the reaction vessel through an inlet tube 16. A quartz enclosure 21 is mounted to the upper electrode as an isolator to isolate the conductive shaft of the upper electrode 19 within an enclosed space 20 and seal it off from the liquid medium within the reaction vessel. A recirculating pump 22 is connected in the inlet tube 16 to drive recirculation of the liquid medium from the bottom of the chamber of the reaction vessel to the top. The pins 23 are mounted in the planar surface of the end piece 8 of the upper electrode and, preferably in a spiral pattern array as discussed further below, and are formed of an electrically conductive material such that electrical discharges (shown for illustration at 24 in FIG. 1) occur between the pins and the adjacent planar surface of the end piece of the lower electrode. Channels or conduits 25 are formed in the end piece of the lower electrode to allow recirculation of fluid through the end piece into the space between the upper and lower electrodes. A valve 27 is connected to the supply line 16 to allow discharge of the fluid medium within the chamber after treatment has been completed.

As noted above, the reactor of FIG. 1 is composed of a cylindrical glass chamber 7, which functions as the reaction vessel, provided with two, stainless steel, upper and bottom caps 9, 17, and a cooling jacket 4. The rotating, cylindrical stainless steel, upper electrode 19 is equipped with the quartz jacket 21 for avoiding the penetration of the reaction media to the electrode sustaining central shaft and bearings. The upper electrode has a cylindrically-shaped, disc cross-section end piece 8, which is terminated in an interchangeable ceramic pin-array holder 29 for the pins 23. Preferably, the pins are spirally located in the pin-array. As used herein, "pin" refers to any type or shape of protuberance extending from the face of the end piece of the electrode. The lower electrode is hollow, and has also an interchangeable conical cross-section end piece, and in addition it is provided with channels 25 for the recirculation of the reaction media. Both the pin-array and the interchangeable metallic part of the lower electrode may be made of various conductive materials, including pure silver. The distance between the pin-array and the lower electrode can conveniently be modified by a micrometric (thimble) screw-system. A typical gap distance is at least about 0.2, preferably at least about 0.5 mm, up to about 3, preferably up to about 1 mm. The distance is selected according to the dielectric constant of the liquid medium. The reactor is vacuum-tight and the rotation of the upper electrode is assured through a magnetic coupling system 15, 18 that couples a motor 13 (e.g., an electric motor, hydraulic motor, etc.) to the upper electrode 19 to selectively drive it in rotation. The reactor can be operated in a batch-type or continuous-flow modes, depending on the specific application. Reactive or inert gases can also be introduced into the dense medium during the plasma processes through the hollow lower electrode. These gases provide bubbles within the planar gap between the electrodes, thereby facilitating the plasma reaction. The rotation of the upper electrode is digitally controllable in the range of 0–5,000 rpm. The rotation of the upper electrode causes further bubble formation through cavitation of the liquid medium. The bubble formation (cavitation) is very important to the efficiency of the dense medium reactor in that the bubbles render a volume-reaction (i.e., the reaction occurs within the volume of the bubble) rather than an interphase reaction.

The colloidal dispersions are made as follows. References are to FIG. 1.

First, the reaction vessel 7 of the dense medium plasma reactor is optionally cooled by recirculating cooling agents 6 such as gas or liquid nitrogen, or cooled alcohol, through the mantle area located between the glass cylinders 4 and 7 of the double-walled reaction vessel. Next, the reaction vessel 7 is charged with a dense-medium reactant material. Upon charging the reaction vessel 7, a positive supply of gas is introduced into the reaction vessel 7 through the lower port 12 contained in the lower static electrode 10. The gas may be various inert gases, one example of which is argon, or reactive gases, examples of which are oxygen, ammonia and $CF_4$. Many other gases may be used depending on the desired reactions between the electrodes. The gas travels through the lower hollow shaft of the lower static electrode 10, through the small central opening located at the upper end of the lower static electrode 10, and then through the dense medium. The gas then forms a gas blanket over the dense medium. The gas blanket may be vented to the atmosphere to accommodate the positive supply of gas that is being introduced through the lower static electrode 10, thereby maintaining the system at the desired pressure, preferably atmospheric pressure. Higher pressure conditions combined with low temperatures can also be used for more volatile dense media such as silicon tetrachloride and isobutylene.

Once the system has achieved low temperature and atmospheric pressure conditions, the upper rotatable electrode 19 is rotated at a high speed, e.g., at least about 50, preferably at least about 500, more preferably at least about 1000 up to about 5,000, preferably up to about 2000 rpm, which results in the recirculation 25 of the dense medium. A direct electric current is then established between the upper planar electrode face of the upper rotatable electrode 19 and the lower planar electrode face of the lower static electrode 10. The direct electric current ignites the plasma reaction. More importantly for this invention the direct electric current, coupled with the rotation of the upper electrode, produces multiple electric pulses. These electric pulses provide the energy to sputter off small particles of the conductive material from the electrodes. The sputtered particles initially may have an electric charge but are believed to rapidly lose that charge to surrounding materials.

Preferably, the voltage applied across the electrode faces is in the range of 100 to 800 Volts, more preferably about 100 to about 250, most preferably about 200 V. The higher voltage peaks (e.g., 250–300 V) applied to the electrodes at the starting point (i.e., the first moment of voltage application) decreases to 100–250 V during the reaction, which is determined by the conductivity of newly synthesized compounds, and the DC current stabilizes between the limits of 0.1–4 Amps. This results in a power range of 10–1000 Watts. By establishing a low electric current to the electrode faces and rapidly rotating the upper planar electrode face relative to the lower planar electrode face without touching the stationary lower planar electrode face, the electric discharge or discharges are initiated in different locations of the plasma zone, i.e. different locations within the planar gap, thereby eluding the creation of local caloric energy concentrations. As a result, the reaction mechanisms produced from the inventive method and apparatus for forming nanoparticles of conducting particles are controlled by electron flux intensity rather than thermal energy.

The dense medium is preferably circulated between the upper and lower planar electrode faces because the plasma reaction and sputtering only occurs in the planar gap located between the electrode faces. The circulation of the dense medium results from the centrifugal force created by the rotation of the upper planar electrode face relative to the lower planar electrode face. This centrifugal force causes the dense medium located between the electrode faces to move radially outward (away from electrode faces). The radial outward movement of the dense medium creates vacuum and cavitation effects which draw more dense medium from within the reaction vessel 7 in the direction of arrows 25 through a plurality of ports 28 located in the lower static electrode 10, into the hollow shaft of the electrode 10, and through the openings of the lower static electrode 10 to the planar gap located between the electrode faces.

The rotation of the upper rotatable electrode 19 also aids in circulating the dense medium contained within the reaction vessel 7. The same centrifugal force created by rotating the upper planar electrode face in relation to the lower planar electrode face causes some of the dense medium located in the planar gap between the electrode faces to gravitate into the lower portion of the reaction vessel 7. This gravitation of the dense medium subsequently forces the dense medium to recirculate from a lower site within the reaction vessel 7 to an upper site within the reaction vessel 7 via the reactant recirculation line 16 and peristaltic pump 22 which comprises part of the dense medium plasma reactor. In summary, the centrifugal force created by rotating the upper rotatable electrode 19 induces a very intense movement and mixing of the dense medium.

The rotation of the upper rotatable electrode 19 permits the fast removal of active species from the plasma zone, i.e., that area which constitutes the planar gap located between the electrode faces, thereby inhibiting the development of extensive decomposition reactions. The rapid circulation also removes the nanoparticles from the area between the electrodes thereby decreasing the possibility of the nanoparticles reattaching to the electrodes. In addition, the rotation of the upper rotatable electrode 19 aids in the achievement of a caloric energy equilibrium of the dense medium.

The finished colloidal dispersion of electrically conducting nanoparticles may be discharged from the dense medium plasma reactor by any convenient means. For example, for batch dense medium reactors, a drain port and valve may be located on the bottom of the reaction vessel 7 to allow the finished colloidal dispersion to be drained into any convenient collection vessel. In another example, for a continuous dense medium plasma reactor, the discharge port may be located on the upper surface of reaction vessel 7 and the colloidal dispersion removed as overflow from the reactor vessel. The small size of the nanoparticles permits the forces of Brownian motion to maintain the nanoparticles and dispersion rather than settling out of the dispersion.

The temperature of the system and, therefore, the temperature of the material contained within the reaction vessel 7, may be monitored and controlled by a thermostat.

The method for producing nanoparticles of electrically conducting materials by means of an induced plasma state may also be carried out as a continuous flow-system reaction. This can be achieved by selecting the proper residence times of dense media in the reactor and employing circulation means, e.g., a peristaltic pump, to circulate the dense medium in and out of the reaction vessel via input and output lines which are connected to the reaction vessel.

The continuous method for producing nanoparticles of electrically conducting materials may also be carried out in a multi-stage plasma reactor. Such a multi-stage plasma reactor comprises multiple dense medium plasma reactors as described above connected either in series or parallel, preferably in series. In the preferred series multi-stage reactor, the output of the upstream reactors is connected to the input of the downstream reactors. An example of such a multi-stage reactor is shown in FIG. 2.

Figure 2:
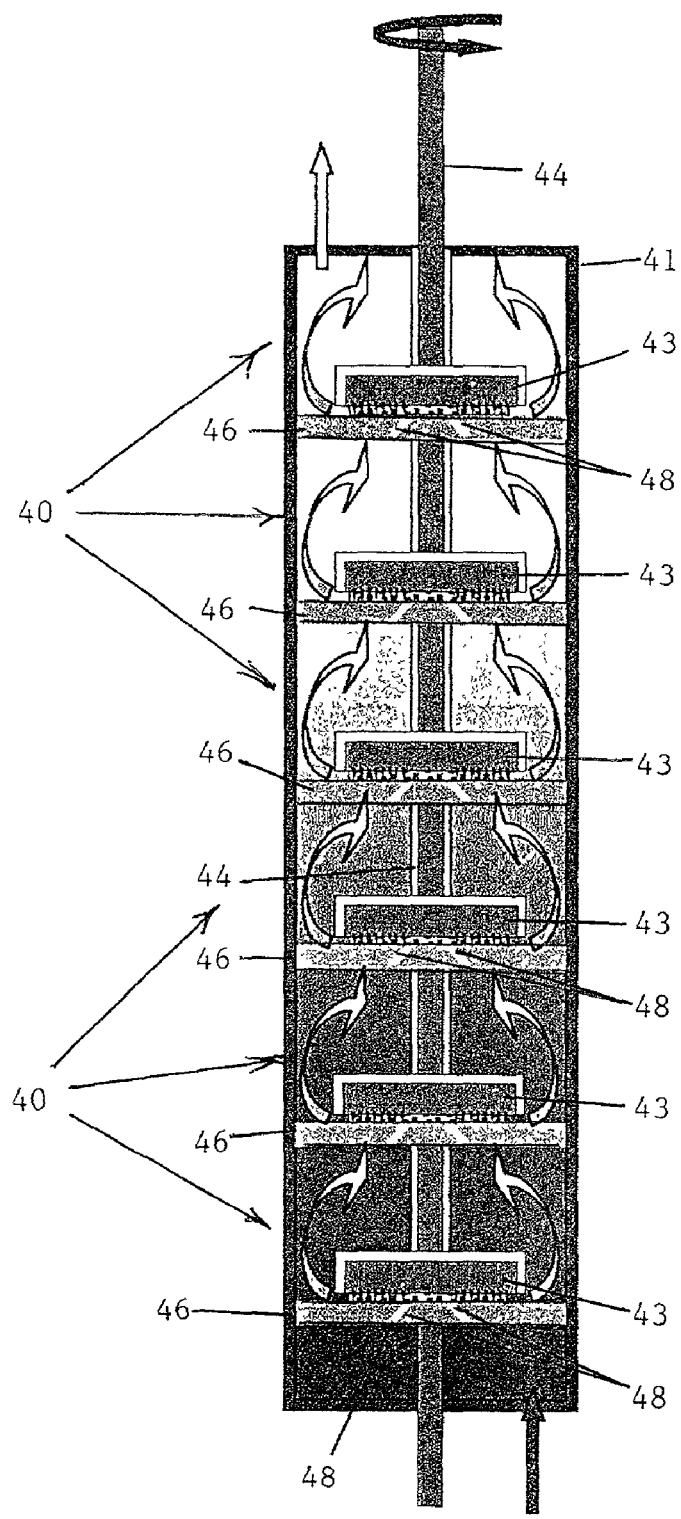
FIG. 2 shows a multistage dense medium plasma reactor suitable for use in continuous production of a colloidal dispersion of nanoparticles.

In FIG. 2 six dense medium plasma reactors 40 are stacked one above the other to form six stages enclosed within an enclosed reaction vessel 41. The rotating electrodes 43 are all attached to a common shaft 44 and therefore rotate at the same speed with respect to stationary electrodes 46 which have openings 48 therein to allow the fluid medium to flow into the space between the upper and lower electrodes. The dense media is introduced to this multistage reactor through an inlet on the bottom of the reactor. The dense media flows through the conduits 48 in the first stage static electrode 48 into the center area of the planar gap between the first stage static electrode 48 and the first stage rotating electrode 43. The plasma reaction, electrode sputtering and dense media circulation occur within the first stage of the reactor as described above for the single stage plasma reactor. The dense media from the first stage of the plasma reactor, bearing an amount of the colloidal dispersion of nanoparticles comprising the electrically conducting material of the electrodes, exits the first stage and enters the second stage of the reactor through conduits in the second stage static electrode. The conduits in the second stage static electrode also introduce the dense media to the center of the planar gap between the second stage static electrode and the second stage rotating electrode. This process is repeated for each stage of the multi-stage reactor. The finished colloidal dispersion of nanoparticles may be collected from the final stage of the multistage reactor. Conveniently, such collection is by means of an overflow discharge from the top of the last stage of the multistage reactor.

The following examples are offered by way of illustration and not by way of limitation.

EXAMPLES

Colloidal dispersions of silver were made in a reactor as shown in FIG. 1. Both electrodes were made of 99.9% pure silver. In a typical "stationary" -experiment 0.5 liter of ACS grade water (available from Aldrich Chemicals) is introduced into the system, then an about 1 mm distance between the electrodes is established, and the rotation of the upper electrodes is initiated and sustained at about 1000 rpm. An argon gas flow rate (0.2 slm) is passed through the liquid medium during the process to degas the water. In the next step, the discharge started and sustained at the 200 DC voltage, 2.5 A electric current and various treatment times between 5 seconds and 5 minutes. The temperature of the dense medium in the reaction system was 15° C. At the end of the reaction the power supply is disconnected from the system and the liquid is removed and stored until analytical work is initiated.

Gravimetric concentration evaluation of the colloidal silver indicates that the silver concentration is about 200 ppm for a 1 minute treatment time.

Figure 3:
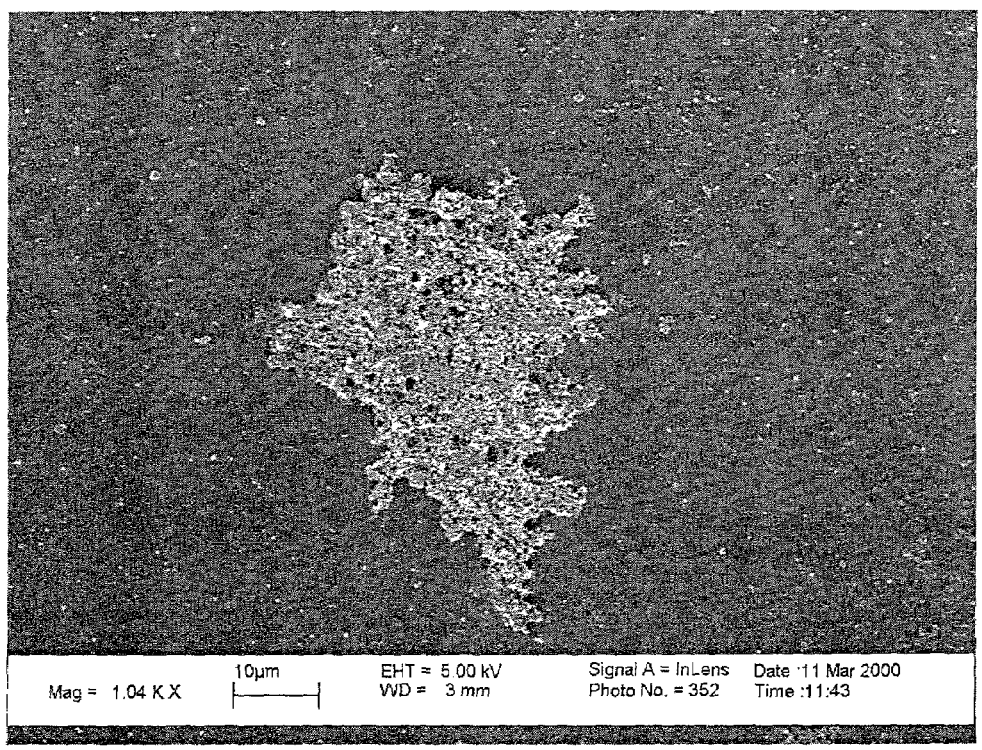
FIG. 3 is a photomicrograph of a dried agglomeration formed from a colloidal suspension of this invention at a magnification of 1040×.
Figure 4:
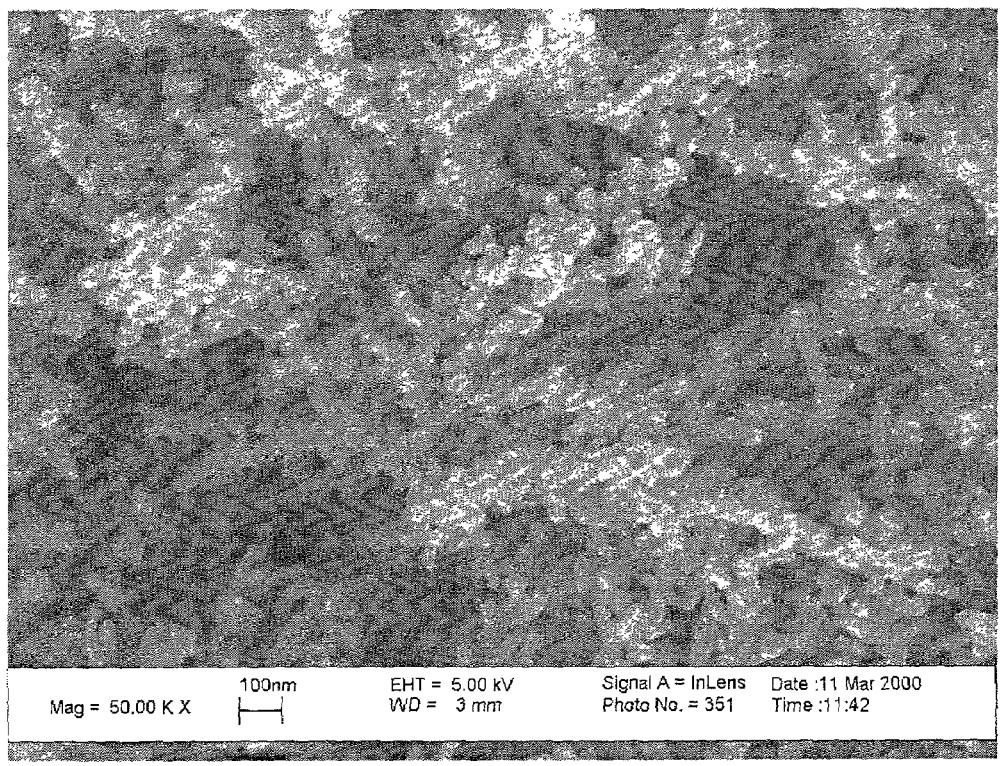
FIG. 4 is a photomicrograph of the same agglomerate as FIG. 3 at a magnification of 50,000×.
Figure 5:
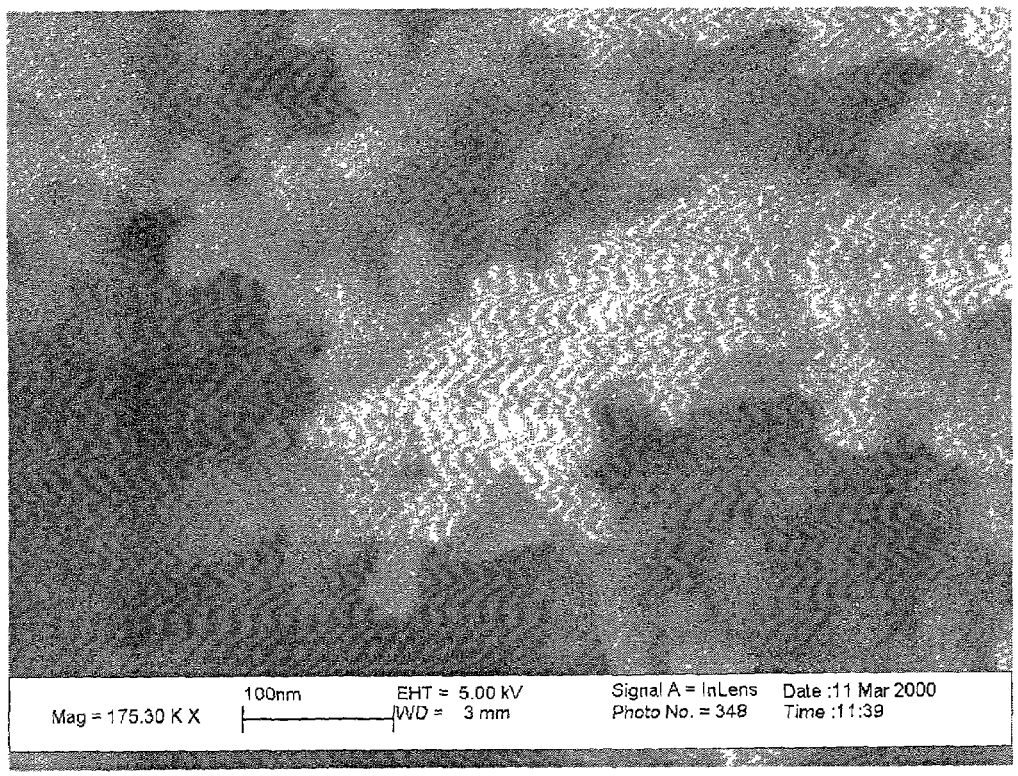
FIG. 5 is a photomicrograph of the same agglomerate as FIG. 3 at a magnification of 175,300×.

The colloidal dispersions produced above were evaporated and the nanoparticles analyzed by scanning electron microscopy and energy dispersion spectroscopy. The results are shown in FIGS. 3, 4, and 5 for magnifications of 1,040×, 50,000× and 175,300×, respectively. The different magnifications permit better evaluation of the particle size variations and shapes. These photomicrographs show particles with dimensions less than 10 nm.

Example 2 Antimicrobial Activity

The antimicrobial activity of colloidal dispersions of silver as made by the current invention were measured. Bacterial contaminated water solutions were prepared and treated either by processing through the dense media plasma reactor or by adding a solution that was processed through the dense media plasma reactor.

The bacterial contaminated water solutions and the plate counts of surviving bacteria have been carried out at the Food Research institute-UW according to the following procedure:

Inoculum for Water Contamination

Four bacterial strains were grown overnight in trypticase soy broth (TSB) at room temperature. The next day they were transferred to TSB (diluted 1:100 in distilled water) and grown overnight at room temperature. The stains were pooled and inoculated into water from Milipore.

Bacterial stains used were two Pseudomonas fluorescens; a *Salmonella typhimurium* and an *Etrobacter agglomerans*.

Procedure for Testing Survival of Bacteria.

Bacteria-contaminated water solutions were treated under the DMP-plasma conditions for different time intervals (Table 1).

After plasma-treatment, the samples were directly plated or diluted in phosphate buffered saline and then plated on Trypticase soy agar. The plated were incubated at room temperature for 72 hours. To test for injured bacteria, 0.5 ml of each sample was added to 4.5 ml of SB and incubated at room temperature.

Survival Results

TABLE 1

Antimicrobial Activity of Colloidal Silver Dispersion

| # | Sample | DC voltage (V) | DC current (A) | Time (s) | Plate Counts of surviving bacteria (log CFU/ml) | Plate counts of surviving bacteria (CFU/ml) |
|---|---|---|---|---|---|---|
| C.S.1 | Initial inoculum of water | — | — | — | 5.73 | 537,032 |
| C.S.2 | Water held until treated samples were plated | — | — | — | 5.41 | 257,040 |
| Ex. A | Bacteria samples treated for 5 s | 200 | 0.4 | 5 | <1.0 | 0. |
| Ex. B | Bacteria sample treated for 10 s | 200 | 0.4 | 10 | <1.0 | 0. |
| Ex. C | Bacterial sample treated for 1 min | 200 | 0.4 | 60 | <1.0 | 0. |
| Ex. D | Water ACS treated and added 1:1 to bacteria sample | 200 | 0.4 | 60 | <1.0 | 0 |
| Ex. E | 1 ml of bacteria sample treated for 10 s added to 200 ml untreated bacteria sample | — | — | — | 3.69 | 4,898 |

In all solutions resulting from the plasma-treatments the bacteria were totally killed. Even solutions prepared from 200 ml, initial "living-bacterial soup" and 1 ml of solution of the 10 seconds plasma-treated bacterial soup exhibited a 99% reduction of the living bacterial content. The only samples that were positive for growth upon enrichment were the untreated water and untreated water with 1 ml of 10 seconds treated bacterial soup.

Treatment of the samples, even for 5 seconds, killed the bacterial inoculum. No bacteria were recovered either by direct plate count or by enrichment. Addition of the 10 second treated bacterial solution to the untreated inoculated water efficiently reduced the bacterial count by 98.1%

This high efficiency of colloidal silver and silver oxide production, and the extremely strong bactericide character of the plasma-generated solutions, allow the development of technologies in a continuous-flow-system mode, and the generation silver-based solutions in high volume liquid media. Such solutions may also be used to kill or control other micro-organic matter such as viruses and spores.

Examples of technologies that are enabled by the inventive method include industrial cooling water applications, air conditioning (especially swamp air conditioners), and swimming pools. Industrial cooling water, in particular cooling water used in the food processing industry, may contain harmful microbes which could contaminate the food. Likewise, air conditioners, such as swamp air conditioners, have been linked to various diseases such as Legionnaires' disease. The results shown in the microbial example indicate that a colloidal dispersion produced by 10 seconds treatment in the dense medium plasma reactor is effective in killing bacteria even after a 200:1 dilution. Therefore, the reactor described above, which processes one-half liter of water into a colloidal dispersion of silver in 10 seconds would, in continuous flow operation, provide 180 liter/hr of colloidal silver which at a 200:1 dilution could sterilize 36,000 liter/hr of contaminated water. This processing rate can easily be increased by building larger dense media plasma reactors or by building multi-stage plasma reactors.

It is understood that the invention is not confined to the particular embodiments described herein, but embraces all such forms thereof as come within the scope of the following claims.

What is claimed is:

1. A method for producing a colloidal dispersion of nanoparticles of at least one conductive material in a dense fluid medium, the method comprising the steps of:
    (a) providing a reaction vessel for containing the dense fluid medium;
    (b) charging the dense fluid medium into the reaction vessel;

(c) providing a rotatable first electrode comprising a first conductive material and terminated in a ceramic pin-array holder, the rotatable first electrode having (i) an end piece with a planar surface and (ii) an array of pins mounted in the pin-array holder and the planar surface; the first electrode immersed within the dense fluid medium;

(d) providing a static second electrode comprising a second conductive material and having a planar surface, the second electrode immersed within the dense fluid medium and being near to the first electrode;

(e) rotating the first electrode such that the dense medium is circulated between the first and second electrodes; and (f) imposing an electric potential between the rotating first electrode and the second electrode to create electrical discharges between the pins and the planar surface of the second electrode, the electric potential being sufficiently high to dislocate nanoparticles of at least one of the first conductive material or the second conductive material from the respective electrode.

2. The method of claim 1 including the step of passing a gas through the discharge zone.

3. The method claim 2 wherein the gas is a reactive or inert gas.

4. The method of claim 1 wherein the second electrode is hollow and includes at least one conduit for passage of the dense fluid medium.

5. The method of claim 1 wherein at least one of the first conductive material or the second conductive material comprises an electrical conductor selected from the group consisting of metals, carbon or combinations thereof.

6. The method of claim 1 wherein at least one of the first conductive material or the second conductive material comprises an electrical conductor selected from the group consisting of aluminum, antimony, bismuth, carbon, copper, gold, iron, lead, molybdenum, nickel, platinum, silver, tin, tungsten, zinc, rare earths or combinations thereof.

7. The method of claim 1 wherein at least one of the first conductive material or the second conductive material comprises silver.

8. The method of claim 1 wherein the nanoparticles have an average diameter of less than about 100 nm as determined by scanning electron microscopy.

9. The method of claim 1 wherein the nanoparticles have an average diameter of less than about 50 nm as determined by scanning electron microscopy.

10. The method of claim 1 wherein the nanoparticles have an average diameter of less than about 20 nm as determined by scanning electron microscopy.

11. The method of claim 1 wherein the nanoparticles have an average diameter of less than about 10 nm as determined by scanning electron microscopy.

12. The method of claim 1 wherein the first electrode rotates at a speed of up to about 5000 RPM.

13. The method of claim 12 wherein the first electrode rotates at a speed of at least about 1000 RPM.

14. The method of claim 1 wherein the planar surface of the first electrode is substantially parallel to the planar surface of the second electrode.

15. The method of claim 14 wherein the pins and the planar surface of the second electrode are separated by a gap of about 1 mm.

16. The method of claim 14 wherein the planar surface of the first electrode and the planar surface of the second electrode are each disk shaped.

17. The method of claim 1 wherein the pins are arrayed in a spiral pattern.

18. The method of claim 1 wherein the distance between the pins and the second electrode is about 0.5 mm.

19. The method of claim 1 wherein the electric potential is about 200 DCV.

20. The method of claim 1 wherein the conductive material of both the first electrode and the second electrode comprises silver and the nanoparticles have an average diameter of less than about 20 nm as determined by scanning electron microscopy.

21. The method of claim 1 wherein the dense medium comprises water with bacteria therein and the method is carried out for a time sufficient to kill the bacteria.

22. A method of producing colloidal nanoparticles comprising:

(a) providing a dense medium plasma discharge apparatus comprising:

(1) a chamber forming a reaction vessel for a dense medium;

(2) a first electrode mounted for rotation about an axis in the chamber having an end piece of conductive material with a planar surface, the first electrode terminated in a ceramic pin-array holder;

(3) a plurality of pins in an array projecting from the planar surface and mounted in the ceramic pin-array holder and the planar surface of the first electrode;

(4) a second electrode mounted in the chamber and having an end piece of conductive material with a planar surface;

the planar surfaces of the end pieces of the first and second electrodes separated from each other by a gap;

(b) immersing the first and second electrodes in a dense medium;

(c) rotating the first electrode with respect to the second electrode; and (d) imposing an electrical potential between the first electrode and the second electrode to create electrical discharges between the pins and the planar surface of the second electrode to form nanoparticles between the first and second electrodes.

23. The method of claim 22 including the step of passing a gas through the discharge zone.

24. The method of claim 22 wherein the gas is a reactive or inert gas.

25. The method of claim 22 wherein at least one of the first electrode conductive material or the second electrode conductive material comprises an electrical conductor selected from the group consisting of metals, carbon or combinations thereof.

26. The method of claim 22 wherein the nanoparticles have an average diameter of less than about 100 nm as determined by scanning electron microscopy.

27. The method of claim 22 wherein the nanoparticles have an average diameter of less than about 50 nm as determined by scanning electron microscopy.

28. The method of claim 22 wherein the pins of the first electrode are arrayed in a spiral pattern.

29. The method of claim 22 wherein the distance between the pins and the second electrode is about 0.5 mm.

30. The method of claim 22 wherein the pins and the end piece of the second electrode are formed of silver and the nanoparticles are silver nanoparticles.

31. The method of claim 30 wherein the dense medium comprises water with bacteria therein and the method is carried out for a time sufficient to kill the bacteria.

32. The method of claim 30 further including the step of adding the silver nanoparticles to water contaminated with bacteria to kill the bacteria.

33. A method for producing a colloidal dispersion of nanoparticles of at least one conductive material in a dense fluid medium, the method comprising the steps of:
(a) providing a reaction vessel for containing the dense fluid medium;
(b) charging the dense fluid medium into the reaction vessel;
(c) providing a rotatable first electrode comprising a first conductive material and terminated in a ceramic pin holder, the rotatable first electrode having (i) an end piece with a planar surface and (ii) at least one pin made of the first conducting material mounted in the ceramic pin holder and the planar surface of the first electrode; the first electrode immersed within the dense fluid medium;
(d) providing a static second electrode comprising a second conductive material and having a planar surface, the second electrode immersed within the dense fluid medium and being near to the first electrode, wherein the planar surface of the first electrode is substantially parallel to the planar surface of the second electrode;
(e) rotating the first electrode such that the dense medium is circulated between the first and second electrodes; and
(f) imposing an electric potential between the rotating first electrode and the second electrode to create electrical discharges between the pins and the planar surface of the second electrode, the electric potential being sufficiently high to dislocate nanoparticles of at least one of the first conductive material or the second conductive material from the respective electrode.

* * * * *